US00PP27417P3

(12) United States Plant Patent
Egger

(10) Patent No.: US PP27,417 P3
(45) Date of Patent: Nov. 22, 2016

(54) ×*HEUCHERELLA* PLANT NAMED 'HOT SPOT'

(50) Latin Name: ×*Heucherella* hybrid
Varietal Denomination: Hot Spot

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 74 days.

(21) Appl. No.: 14/545,242

(22) Filed: Apr. 13, 2015

(65) Prior Publication Data

US 2016/0302346 P1 Oct. 13, 2016

(51) Int. Cl.
*A01H 5/12* (2006.01)

(52) U.S. Cl.
USPC ..... Plt./441

(58) Field of Classification Search
USPC ..... Plt./441
See application file for complete search history.

(56) References Cited

PUBLICATIONS

Greenhouse Management 2014. Terra Nova announces new Heucherella, retrieved on Aug. 16, 2016, retrieved from the Internet at <http://www.greenhousemag.com/article/terra-nova-hot-spot-2014-sneak-peek/> pp. 1-3.*

* cited by examiner

*Primary Examiner* — June Hwu
(74) *Attorney, Agent, or Firm* — Klarquist Sparkman, LLP

(57) ABSTRACT

A new and distinct ×*Heucherella* plant substantially as shown and described, characterized by a low, spreading habit, a *Heuchera*-like leaf shape, leaves of yellow to lime green in color with a large red brown center spot, showy dark pink flowers from spring to fall, and excellent vigor.

1 Drawing Sheet

Botanical denomination: ×*Heucherella* hybrid.
Variety designation: 'Hot Spot'.

BACKGROUND

The present invention relates to a new and distinct cultivar of ×*Heucherella* and given the cultivar name of 'Hot Spot'. ×*Heucherella* is in the family Saxifragaceae. ×*Heucherella* 'Hot Spot' originated from a controlled cross between a proprietary unreleased, unpatented seedlings *Heuchera* 'K842-5', as the seed parent, and *Tiarella* '42-2', as the pollen parent.

Compared to the seed parent *Heuchera* 'K842-5', the new cultivar is trailing rather than clumping and has yellow green to lime green leaves with a red brown center spot rather than red brown leaves.

Compared to *Tiarella* '42-2', the new cultivar has yellow to lime leaves rather than green.

Compared to ×*Heucherella* 'Yellowstone Falls', U.S. Plant Pat. No. 22,313, the new cultivar has showy pink flowers rather than white, a large dark center spot rather than a splatter patter, and less leaf lobing.

Compared to ×*Heucherella* 'Stoplight', U.S. Plant Pat. No. 16,835, the new cultivar is larger, trailing rather than clumping, and has showy pink flowers rather than white.

This new ×*Heucherella* is unique in having the following characteristics:

1. a low, spreading habit,
2. a *Heuchera*-like leaf shape,
3. leaves yellow to lime green in color with a large red brown center spot, 4. showy dark pink flowers from spring to fall,
5. and excellent vigor.

This new cultivar has been reproduced only by asexual propagation (division and tissue culture using growing tips). Each of the progeny exhibits identical characteristics to the original plant. Asexual propagation in 2013 by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a nine-month-old ×*Heucherella* 'Hot Spot' in a one gallon container grown outdoors in the shade in flower in June in Canby, Oreg.

FIG. 2 shows a one-year-old ×*Heucherella* 'Hot Spot' grown outdoors in the field shade in flower in September in Canby, Oreg.

DETAILED PLANT DESCRIPTION

The following is a detailed description of the new ×*Heucherella* cultivar based on observations of one and a half-year-old specimen in October growing in one gallon containers outside in the shade in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart,* 5th edition, 2007.

Plant:

*Form*.—Basal rosette and trailing, herbaceous perennial.

*Hardiness*.—USDA Zone 4 to 9.

*Size*.—16 cm tall from top of the foliage to the ground and 42 cm wide.

*Habit*.—Mounding and trailing.

*Vigor*.—Excellent.

*Roots*.—Fibrous, freely branching, fine, and white in color.

Stem:

*Size*.—Grows to 7 mm wide and 16 cm long.

*Internode length*.—0.5 mm to 1.5 mm.

*Stem color*.—Grey Brown 199B near base blending to Greyed Purple 185C near tips.

Leaf:

*Type*.—Simple.

*Arrangement*.—Rosette and alternate.

*Shape*.—Broadly ovate.

*Lobing/division*.—7 shallow palmate lobes with the terminal the longest, each with shallow secondary lobes.

*Venation*.—Palmate, topside Yellow Green 145C, bottom side 145D.

*Margins*.—Crenate, no undulation.

*Apex*.—Mucronulate.

*Base*.—Cordate.

*Glossiness*.—Weak.

*Blade size*.—Grows to 12 cm long and 8.5 cm wide.

*Surface texture*.—Glandular hairs on both sides.

*Petiole description*.—Grows to 13 cm long and 2 mm wide, glandular hairs, Grey Brown 199B tinted Greyed Purple 185C.

*Leaf color*.—Leaves yellow to lime with a dark central spot at the leaf base and follows up the main veins; spring (and fall new growth) topside Yellow Green 145A with dark center spot, Greyed Red 178A; summer topside Yellow Green 144A with the pattern Greyed Red 178A; bottom side spring and summer Yellow Green 146D with spot a muted version of Greyed Purple 187A; fall and winter leaves topside Yellow Green 145A with pattern along veins Greyed Purple 187A, bottom side closest to Yellow Green 147C with pattern a muted Greyed Purple 187A.

Inflorescence:

*Size*.—Grows to 3 cm wide and 16.5 cm long.

*Type*.—Raceme.

*Number of flowers per raceme*.—About 100.

*Number of racemes*.—About 30.

*Attitude*.—Upright to semi-upright.

*Density*.—Medium.

*Peduncle*.—Grows to 26 cm tall, 2 mm wide at base, Greyed Orange 177A, glandular hairs, usually with one side branch and one to two leaves (blades grow to 3 cm long and 3.5 cm wide, usually ovate, coarsely serrate, tip mucronulate, base obtuse, glandular hairs on both sides, topside Yellow Green 146B with very small pattern on largest Greyed Purple 183A, bottom side Yellow Green 146C).

*Pedicel*.—Grows to 9 mm long, with glandular hairs, Greyed Orange 176A.

*Bloom period*.—May to October in Canby, Oreg.

Flower bud:

*Size*.—2 mm wide and 4 mm long.

*Description*.—Glandular puberulent, ovoid.

*Color*.—Red Purple 63B on tip blending to 63D at base.

Flower:

*Type*.—Perfect.

*Shape*.—Campanulate.

*Attitude*.—Side-facing.

*Size*.—11 mm deep and 8 mm wide.

*Petal description*.—5 in number, linear, 4.5 mm long, tip acuminate, base attenuate, margin entire, glabrous on top and glandular hairs on bottom, Red Purple 65D on both sides.

*Calyx description*.—3 mm deep and 7 mm wide, with 5 lobes, divided ½ way to the base, campanulate, glandular hairs on both sides, tip acute, margin entire, back side Red Purple N66C on lobes to 65B on tube, inside Red Purple N66D on lobes to 65B on tube.

*Stamen description*.—10 in number, filaments 3 mm long, Red Purple 65D, anthers sterile, less than 1 mm, Orange Red 35C.

*Pistil description*.—One central two beaked pistil, 6 mm long, White NN155C.

*Fragrance*.—None.

*Lastingness*.—Each raceme blooms for about 3 weeks on the plant.

Fruit and seed: None.

Disease and pest tolerance: The new cultivar is typical to the genus. No known resistances to pests or diseases. No problems have been found in Canby, Oreg.

I claim:

1. A new and distinct ×*Heucherella* plant as herein illustrated and described.

* * * * *

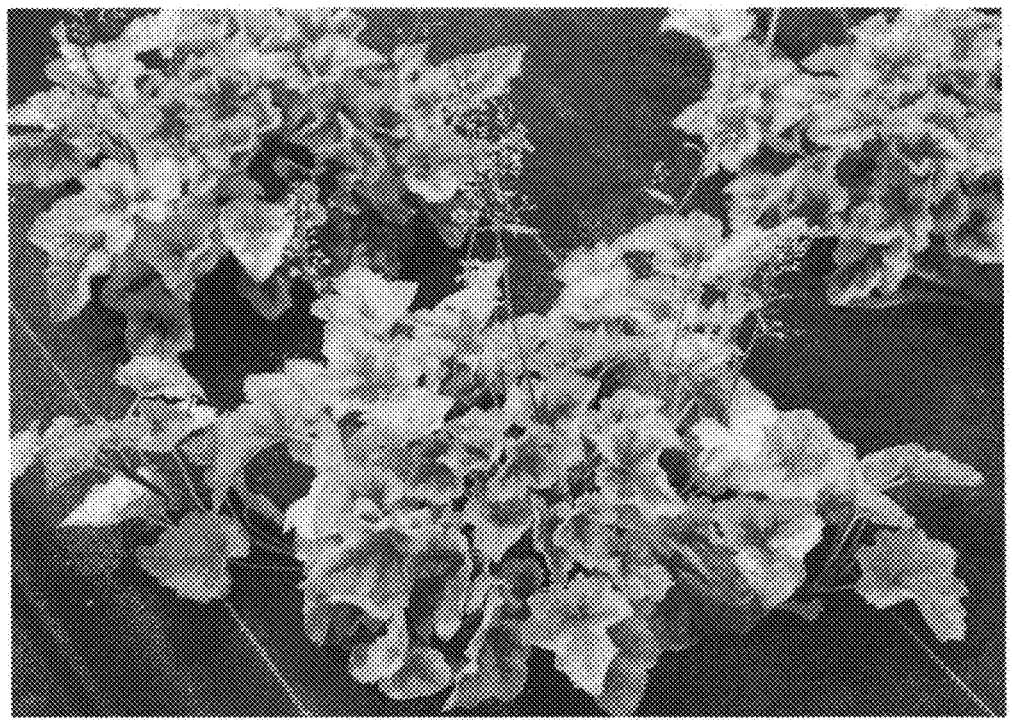

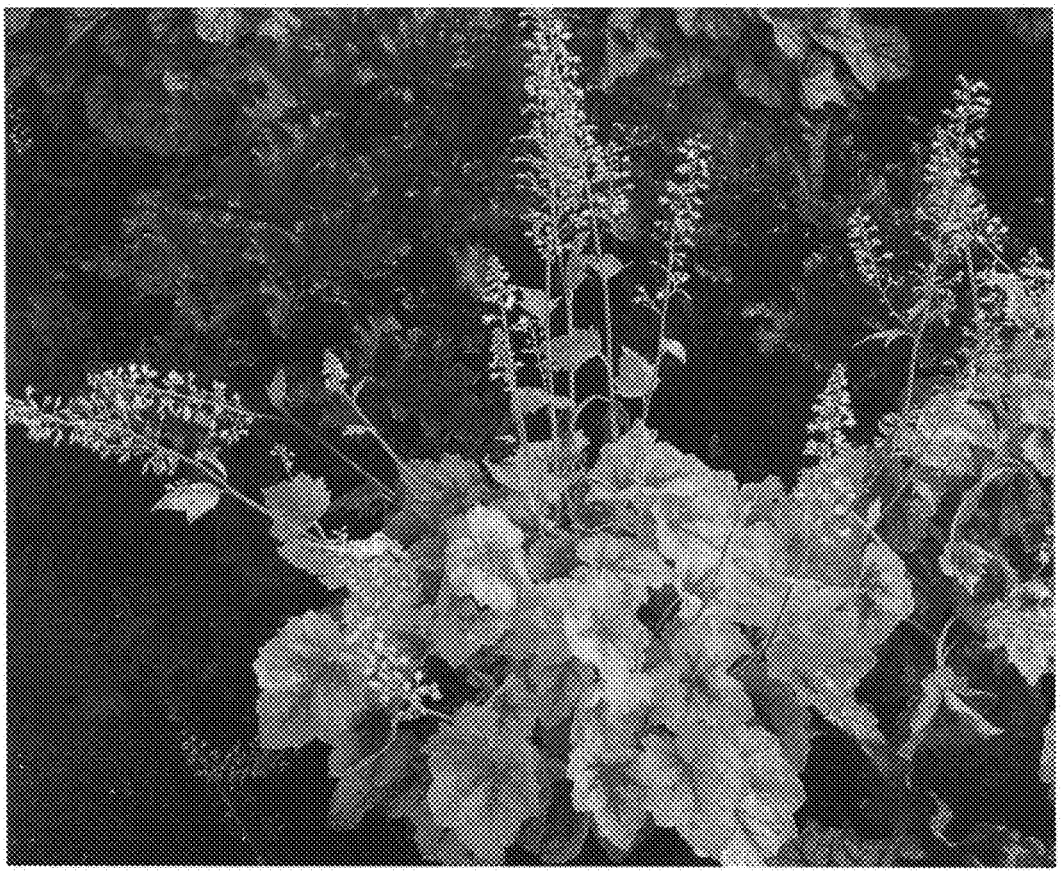
FIG. 1 above, FIG. 2 below